(12) United States Patent
Engman

(10) Patent No.: US 7,309,231 B2
(45) Date of Patent: Dec. 18, 2007

(54) IMPLANT

(75) Inventor: Fredrik Engman, Molnlycke (SE)

(73) Assignee: Neoss Limited (GB)

( * ) Notice: Subject to any disclaimer, the term of this patent is extended or adjusted under 35 U.S.C. 154(b) by 0 days.

(21) Appl. No.: 10/117,310

(22) Filed: Apr. 5, 2002

(65) Prior Publication Data

US 2002/0177105 A1  Nov. 28, 2002

(30) Foreign Application Priority Data

Apr. 5, 2001 (GB) ................................. 0108551.3

(51) Int. Cl.
*A61C 8/00* (2006.01)
(52) U.S. Cl. ........................................ 433/173; 606/73
(58) Field of Classification Search ................ 433/173, 433/174, 172, 175; 606/73, 72
See application file for complete search history.

(56) References Cited

U.S. PATENT DOCUMENTS

| 4,960,381 A | 10/1990 | Niznick | 433/174 |
| 5,195,892 A * | 3/1993 | Gersberg | 433/174 |
| 5,334,024 A | 8/1994 | Niznick | 433/173 |
| 5,584,629 A | 12/1996 | Bailey et al. | 411/178 |
| 5,782,918 A * | 7/1998 | Klardie et al. | 606/60 |
| 5,823,776 A | 10/1998 | Duerr et al. | 433/173 |
| 5,947,733 A | 9/1999 | Sutter et al. | 433/173 |
| 6,116,904 A * | 9/2000 | Kirsch et al. | 433/173 |

FOREIGN PATENT DOCUMENTS

| DE | 19903482 A1 | 8/2000 |
| EP | 0879580 A2 | 11/1998 |
| EP | 1021996 A1 | 7/2000 |
| WO | WO9832393 | 7/1998 |
| WO | WO9852488 | 11/1998 |
| WO | WO0009031 | 2/2000 |
| WO | WO0027300 | 5/2000 |
| WO | WO0054696 | 9/2000 |

OTHER PUBLICATIONS

Kirsch et al. "Camlog Connection-Requirements for Reliable Implant Prosthetic Treatment Concept; Tooth for Tooth Restoration," *Quintessenz* 50, 10, 1-18 (1999).
International Search Report for PCT/GB02/01465, Jul. 2002.
International Preliminary Examination Report dated Jul. 2, 2003 for PCT/GB02/01465.

* cited by examiner

*Primary Examiner*—Melba Bumgarner
(74) *Attorney, Agent, or Firm*—Akerman Senterfitt

(57) ABSTRACT

The present invention is directed to a threaded implant intended to be screwed into bone, preferably into jawbone, and for tightly fitting a prosthesis, including a spacer portion, in the screwed-in position. The implant body has an internal connection arrangement for rotationally locking said spacer, said arrangement also co-operating during positioning and insertion of the implant body with a tool and said arrangement having a low vertical height.

26 Claims, 5 Drawing Sheets

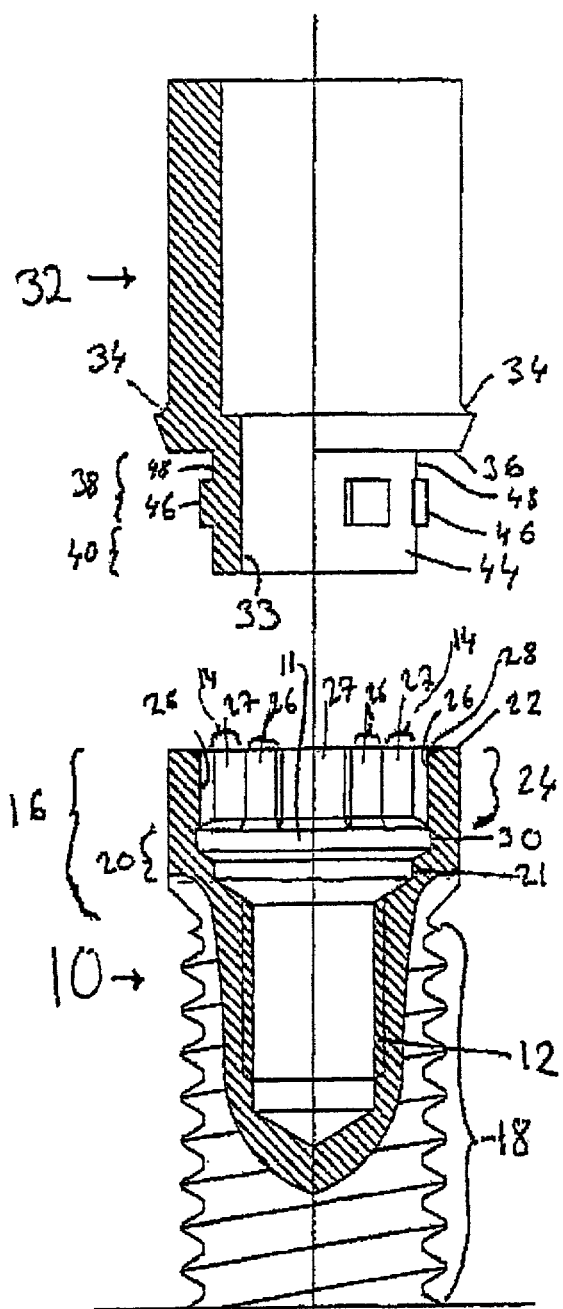

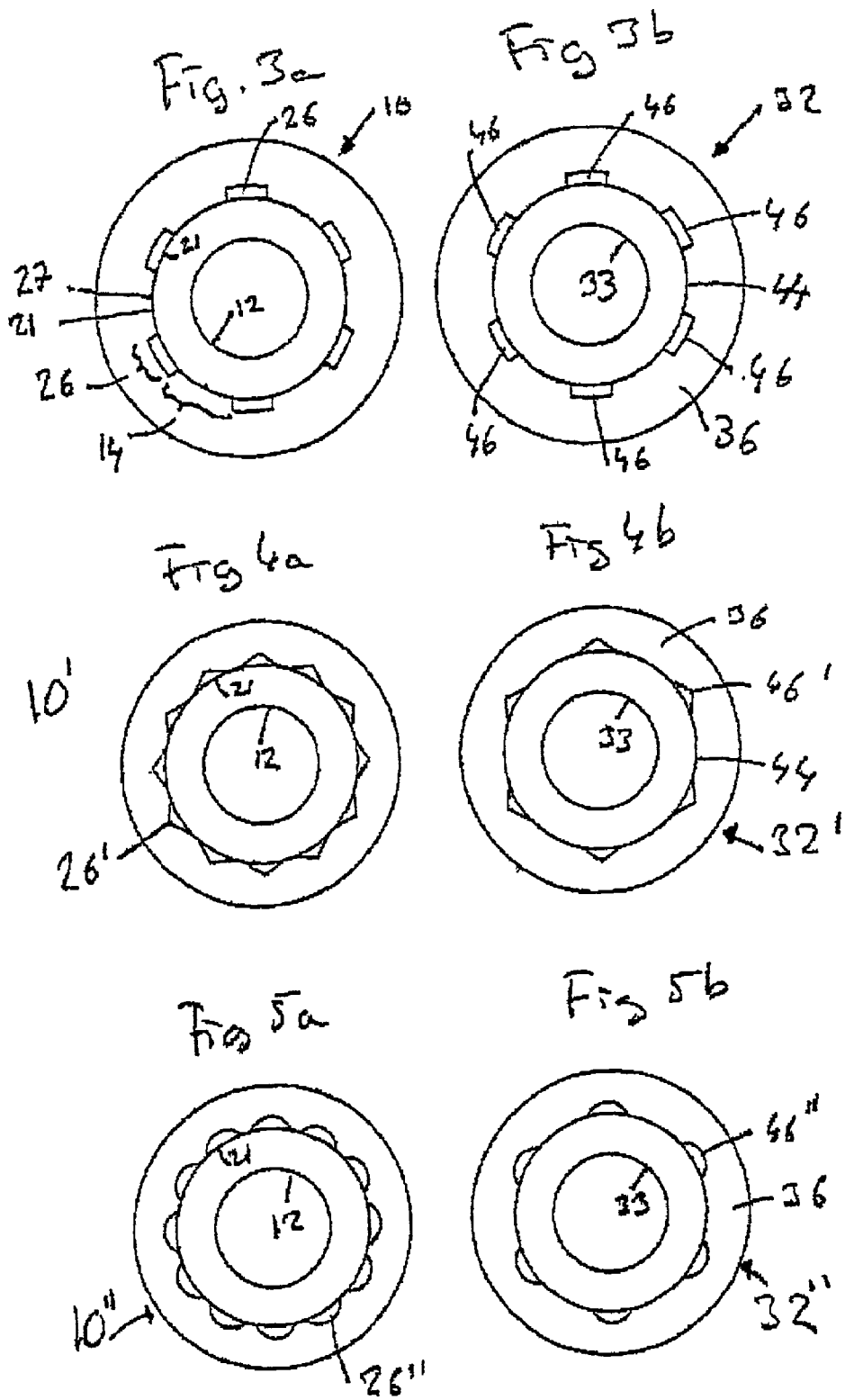

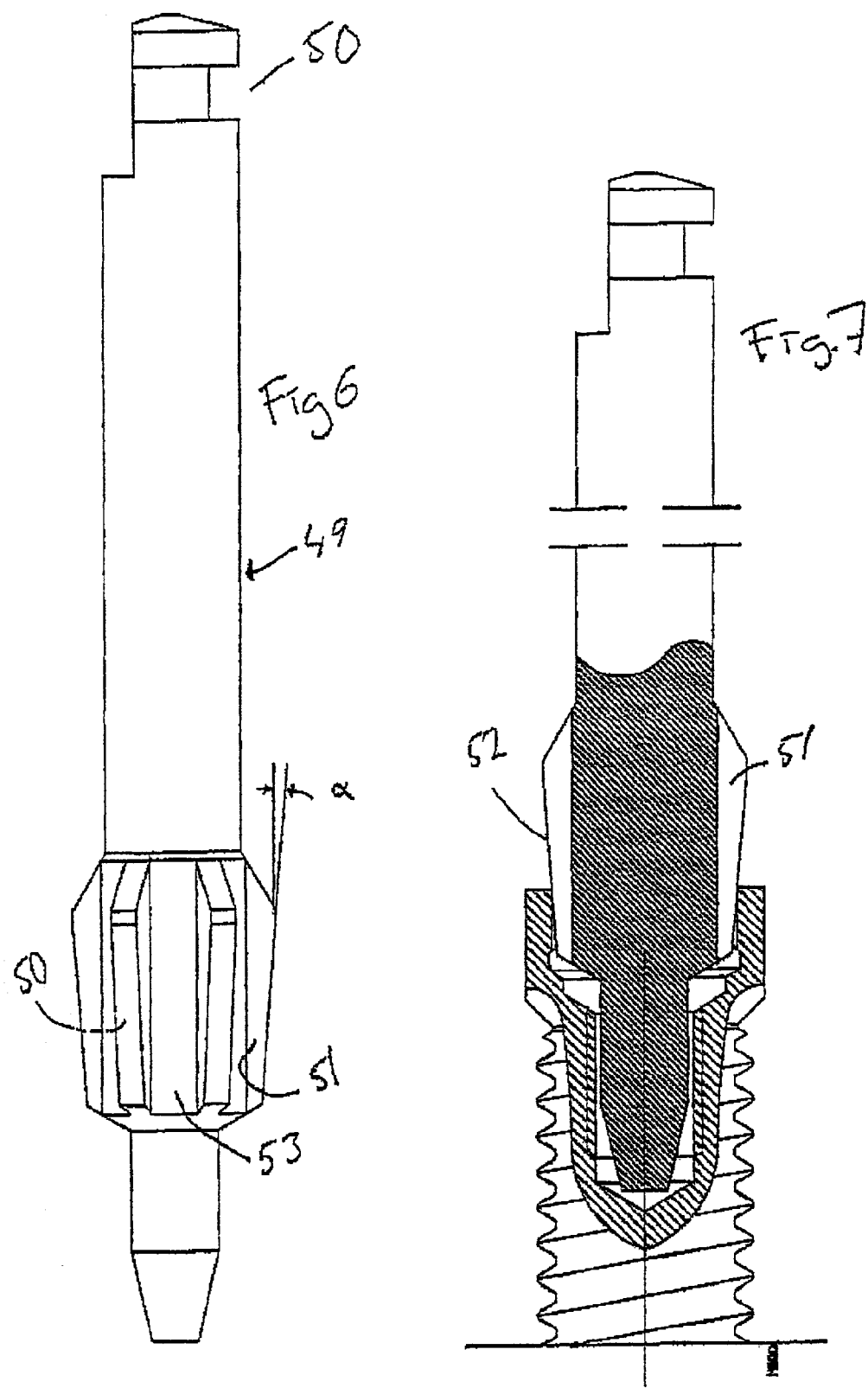

IMPLANT

This application claims the benefit of United Kingdom Patent Application No. 0108551.3, filed Apr. 5, 2001, the disclosure of which is hereby incorporated herein by reference.

The present invention is directed to a novel implant and to a novel method of treatment related thereto.

In particular the invention relates to a threaded implant intended to be screwed into bone, preferably into jawbone, and for tightly fitting a prosthesis, including a spacer portion, in the screwed-in position.

This implant includes an implant body, that is insertable in a hole made in bone and a spacer element attachable to the implant body. The implant body has a blind bore open on one end which is a coronal end and closed at the opposite end. The spacer is attachable in a twisting prevented manner to the coronal end of the implant body and has a centering collar which is insertable into the hollow cylindrical annular recess formed by a blind bore in the implant body adjacent the coronal end while a shoulder of the spacer is received on the outer edge of the body at the corona end. The twisting preventing means for the spacer in the implant body bore can also cooperate with a tool during insertion of the implant body in to the bone. This tool can apart from being an inserter tool also carry the implant body to the hole by internal cooperation with the bore at the coronal end including the twisting prevention means. The invention also relates to an arrangement for a threaded implant body of the said type and to a method for anchoring the implant body in bone, preferably in jawbone.

Implants also intended to be screwed into bone are presented in International Patent Application No WO00/09031. Such implants, are also commercially available products by Nobel Biocare under the name Replace Select, and by Altatec Biotechnologies under the name of the Camlog Implant System. For these implants, the tool and spacer connection element have been combined in a common position inside the implant body and they are commonly delivered with a pre-mounted fixture mount. The arrangement with an internal connection provides easier handling and results in better feedback during the procedure of the prosthetic connection than a conventional external hex arrangement, i.e. Brånemark System. However, International Patent Application No WO00/27300 describes a separated tool and prosthesis "socket", which is a completely different type of connection and thereby implant, namely a type which does not only have a blind bore projecting inwards from the coronal end according to the above, but can be provided with a part which projects upwards from the coronal end, i.e. an external hex, which is arranged with a rotational preventing connection for a prosthesis structure and a geometric separate connection for a tool during insertion in to the bone. This also allows a tool to be used in carrying the implant body to the prepared site in the bone and thus excludes the need for fixture mounts, pre-mounted or not. This technique used to insert an implant body instead of using a conventional fixture mount being attached to the implant body during insertion, has recently gained a lot of appreciation and replaced a large number of the conventional fixture mounts being used due to its ease of use.

Yet another completely different type of implant is presented in U.S. Pat. No. 5,823,776, namely a type of which the implant body constitutes of a cylindrical body and thus no external threads. This type of cylindrical implants are however not suitable in all situations and do not provide initial stability within the bone as provided by a threaded implant body.

The internal connection as shown by the prior art references above do not exist in relation to an insertion tool without using a fixture mount pre-mounted or not, which is in contradiction to the implant shown in WO 00/27300. The invention aims to solve this problem among others for an internal connection.

The same type of implant can be used for two-stage or one-stage procedures. The internal connections according to Replace Select and the Camlog Implant System above show a large vertical height, which is not optimal for a two-stage procedure. In addition they all have obtained internal space for the spacer connection deep into the bore by thinning the implant body wall and thus decreasing the strength of the implant body but still the coronal height might exceed an unacceptable level which can lead to penetration of the mucosa and risk for excessive forces and thereby risk of loosing the implant during the healing period. This problem will be dealt with by the provided solution.

A common problem of the internal connection as can be shown by the references above is that the plug of the spacer need to have a sufficient wall thickness and thus influencing the outer and/or inner diameter. This results in either a decrease wall thickness of the implant body, as for the Camlog Implant System, or to less space for an internal spacer screw, as for the Replace system. The first case will lead a weakened implant body and the second to a decreased strength of the spacer connection and a discrepancy in a system where compatibility shall withstand.

The solution described in WO 00/27300 has a weak point in terms of mechanical strength since the wall thickness due to compatibility is bound to be thin. This fact implies high angular tolerances to fit the "internal tool socket" within the external hex, and thus complicated production. Also these points are corrected with the invention.

This lack of space given by the solution described in WO 00/27300 also gives in hand tat the "internal tool sockets" are limited in radial thickness and tangential width and thus strength implying that the insertion tool need to be manufactured in a special grade of stainless steel making the tool expensive.

At very high insertion torque there is always a risk of damaging the small "internal tool sockets" described in WO 00/27300. This solution is dependent on the use of a special high grade c.p. titanium or alloyed titanium, whose clinical effects compared to a lower grade c.p. titanium have been up for debate for years. This is also solved by the invention.

Failure of an implant due to abutment screw loosening and subsequent fatigue fracture of abutment screw and the implant is a real problem in implant treatment. It should be noted that hereinafter that the terms abutment and spacer are used interchangeably. This would be well understood by one skilled in the art. Even though the risk is little (<1% of the cases) the result could be devastating to the patient in terms of physical harm and to the clinician in economical terns. Implant manufacturers have dealt with the problem in different ways.

There are several patents that reflects this work, for example, U.S. Pat. No. 5,947,733 to Straumann, and also commercially available products like the Astra Tech Implants Dental System. The patent describes the use of an internal cone which forms a stiff intersection thus relieving the internal screw bending and tensile stresses and creating a rigid connection in terms of rotational and bending movements and minimizing the risk for screw loosening. However the internal cone technique has received criticism for the final aesthetical result and so far there is no good proposal how to incorporate the internal solution with a functional carrying system, such as the Stargrip system available from Nobel Biocare. In addition the internal cones have too little flexibility during bending and thus the load is transferred directly down to the bone. A natural tooth has an elastic layer, therefore it is desirable to have an implant with some degree of bending flexibility which will distribute the bending forces more evenly. For the most common abutment connection used today, e.g. comprising an external hex fitting, techniques have been proposed, for example, by the 3i "Restorative Catalogue" (nr CATRC Rev.2/00) and by U.S. Pat. No. 5,334,024 to Sulzer Dental, which includes press fit or friction fit and thus extremely high tolerances. These solutions are mainly made to minimise rotational movements and to a less degree the bending movements between the implant and the abutment and thus avoiding screw loosening. The external hexes present at the market today range from 0.6 to 1.0 mm which is too low to avoid excessive bending movements with or with out fine tolerances and/or different fit solutions. As a remark higher hexes would not be suitable due to for example aesthetical reasons.

As stated herein before there exists benefits with internal connections over external connections and one more benefit is a stronger resistance to bending forces. One such internal solution is described in the U.S. Pat. No. 4,960,381 with the preferred embodiment of an internal hex. A possible and obvious solution to increase the resistance to screw loosening would be to add the same features as described above for the external hex. The demand on high tolerances would however remain the same and there is still no solution to incorporate means for the insertion tool to be able to carry the implant.

The design of the deep internal "tube" connection is represented by the previous mentioned Replace Select and the Camlog Implant System, and provides an even stronger resistance to bending than the prior mentioned internal hex. For example the tube design for the Camlog Implant System is claimed in "Camlog Connection—Requirements for reliable implant prosthetic treatment concept; tooth for tooth restoration", Quintessenz 50, 10, 1-18 (1999), to prevent screw loosening by being 100% rotation free and a form and forced based connection. However, this is only achievable by the extreme high tolerances adapted, which is a draw back and also true for Replace Select together with the previous restrictions of this type of deep internal connection.

So for a preferred connection between the prosthetics and the implant, there is no solution with an internal connection that reduces the risk for abutment screw loosening with press- or friction-fit and at the same time benefits from a strong but still controlled flexible abutment connection and relative low tolerances compared to the deep internal "tube" connections.

Therefore, one object of the present invention is to provide an implant wherein the case of a combination of improved insertion handling and prosthetic connection together with ease and cost effectiveness of manufacturing is ensured and at the same time obtaining the highest possible strength of the implant. Furthermore, it is a further object of the present invention to provide an implant system which minimises the demand for high tolerances.

Thus, according to a first aspect of the invention we provide an implant for a tightly fitting prosthesis, said implant comprising;
an externally threaded implant body intended to be screwed into bone using an insertion tool, the body being provided with an internal open ended axial bore and an indexing region at the open end of the bore, the indexing region being provided with a connection to support a spacer element and having means for co-operating with the spacer element to prevent twisting between the spacer element, the implant body and the insertion tool characterised in that that the axial length of the indexing region does not overlap, eg does not substantially overlap, with the external thread.

The indexing region preferentially comprises a positive connection region, a guidance region and a centering region. In particular, the indexing region permits the insertion tool to provide a carrying function for positioning the implant.

To accomplish these objectives, the present invention is directed to an implant having an implant body, a spacer and internal means for preventing twisting therebetween and/or between an insertion tool. In addition, the present invention is directed to an insertion tool with capacity to carry the implant body or parts of it to the prepared site with no other connective forces than introduced by the friction and press-fit between the tool and the implant body. The implant body has a blind bore forming a coronal end for the body and has a positive connection area adjacent the coronal end followed by a combined guide and centering portion with a substantially cylindrical surface and not extending deeper in to the bore than to avoid an overlap of the external thread meaning that between the coronal end of the implant body and the outer thread(s) there is a smooth portion which has a minimal vertical height. Other conventionally known insertion tools do not have such wide applications and/or are adapted to be seated in a protruding part of the implant, whereas in the present invention the insertion seats in the implant itself.

The spacer element used in the implant of the invention is novel per se.

Thus, according to a yet further aspect of the invention we provide a spacer element for use in an implant as hereinbefore described.

The spacer has a fastening end for a prosthetic construction spaced from a plug portion by an annular shoulder. The plug portion adjacent the shoulder has a positive connecting portion on a substantially cylindrical portion followed by a combined guidance and centering portion with a circular cross section, preferably a cylindrical surface. The diameter and length of the cylindrical surface of the guidance and centering portion matches the diameter and length of the guide and centering portion of the blind bore. The means for preventing twisting between the implant body and the spacer, as well as insertion tool, includes positive connecting elements in the positive connecting portion and positive connecting area with the elements including at least three grooves, preferably 6, and at least one projection receivable, preferably 3, in the grooves when the plug portion is inserted into the blind bore with the annular shoulder engaging the end face of the coronal end, thus providing a maximum of 120° direction difference, preferably 60°. The spacer has a bore that extends through the centering collar and is open on its coronal end for the reception of a spacer screw to fastening the spacer to the implant body. The spacer screw will directly or indirectly be insertable into the blind bore of the base and at least partially traverse the spacer and the fastening head for the dental prosthesis.

The co-operating means which is adapted to prevent twisting between the implant body and the insertion tool in one moment and than in another moment the spacer, may comprise means for engagement between the spacer and the implant body or may comprise coincident members which together engage with the insertion tool. Thus, the co-operating means can comprise positive connecting elements in the positive connecting portion and positive connecting area with the elements including at least three grooves and at least three projection receivable in the grooves when the insertion tool is inserted into the blind bore resulting in a high capacity torque connection of up to 100 Ncm and over between the insertion tool and the corresponding positive connecting area of the basic implant body.

Another embodiment of the invention is characterised in that the spacer screw completely traverses the spacer and can be screwed into internal threads close to a cervical or closed end of the implant body.

It is also possible according to the invention for at least one of the implant body positive connection elements to have the form of a coronally open positive connection groove extending parallel to the longitudinal axis of the implant body.

According to a further feature of the invention we provide an arrangement for a threaded implant adapted to permit application of a screwing force for positioning and securing in the implant's screwed-in position, the implant comprising an open ended internal bore; at least one spacer element against a contact surface of the implant, wherein the implant body is provided an indexing region with means for preventing and twisting which can be assigned to both the tool and the spacer element or the tool and the indexing region, characterised in that the axial length of the indexing region does not extend deeper into the bore and does not overlap of the external thread.

In the arrangement of the invention a relatively large force applied, by means of an insertion tool, on the twisting prevention means, is prevented from mechanically affecting the later fitting between the implant body and the spacer element to a non-fitting situation.

According to a yet further feature of the invention we provide a method for anchoring a threaded implant in a bone and applying at least one spacer element to a contact surface if the implant in its screwed-in position, characterised in that the screwing-in is effected by means of a tool which is arranged on a twisting preventing portion provided in the implant and in that this portion also provides a twisting prevention for the spacer element during at least the clinical function.

In the method of the invention, the tool may be arranged against an internal portion of the implant and is designed to ensure bearing function of the implant. The tool may be of a star screwdriver type and may be arranged against an internal person of the implant where, during screwing-in, the winged-shaped parts of the tool are pressed against essentially radially extending surfaces in the twisting prevention means like grooves.

Although the method of the invention may be applied to any bone, it may preferentially be applied to a jaw bone.

The method according to the invention is characterised essentially in that the screwing in effect is effectuated by means of a tool which may be of a winged-shaped star screwdriver type is arranged against an internal portion of the implant where, during screwing-in, the winged-shaped parts or a partly substantially cylindrical portion of the tool are pressed against essentially radially extending surfaces in the twisting prevention means like grooves or any adjacent portion of the internal bore.

The invention also proposes that the positive connection grooves have in a radial plane, which extends perpendicular to the axis of the bore, a basic substantial circular segmental cross section. The positive connection grooves can have a substantially triangular cross section in a radial plane which extends perpendicular to the axis of the bore in the implant body. The invention optionally proposes that the positive connection grooves in a radial plane which extends perpendicular to the axis of the bore in the implant body has an approximately rectangular-curved cross section.

According to the invention the positive connection grooves can be opened toward the closed or cervical end.

It is also possible according to the present invention for the positive connection grooves to have a decreasing cross section from adjacent the coronal end towards the closed end of the implant body. The invention also proposes the cross section of the positive connection grooves decreases radially from the coronal and to the closed end of the implant body. The implant body connection elements can have a 30° spacing with respect to the implant body circumference.

The invention also proposes that the implant body positive connection elements have a 60° spacing with respect to the implant body circumference.

According to the invention it is also possible for the number of positive connection elements of the spacer to be smaller than the number of positive connection elements of the implant body.

Another embodiment of the invention is characterised in that the positive connection area of the implant body has an annular undercut between the positive connection elements of the implant body and the guidance area.

It is also possible according to the present invention for the end wall at the coronal end of the implant body to have a bevel or chamfer tapering conically inward from the front edge of the implant body into the vicinity of the implant body positive connection elements.

The invention also proposes the positive connecting portion of the centering collar has an annular undercut between the shoulder and the connection elements.

A method according to the invention is essentially characterised by that the implant is provided with internal twisting prevention means which can be assigned to both the tool and the spacer element, provided that the combined length of the of the postive connection area and guidance and centering area does not extentially extend deeper into the bore than to avoid an overlap of the external thread, and in that a tool is arranged against an internal portion of the implant and is designed to ensure bearing function of the implant.

Further developments of the method are characterised in that the tool of a star screwdriver type is arranged against an internal portion of the implant body where, during screwing-in, the winged-shaped parts or a partly substantially cylindrical portion of the tool are pressed against essentially radially extending surfaces in the twist prevention means like grooves or any adjacent portion of the internal bore.

In a yet further embodiment of the invention we provide an implant kit comprising;
an implant as hereinbefore described;
a tool adapted for carrying and inserting the implant; and
a spacer element adapted to fit the implant.

The implant kit may also include a spacer screw. Such a kit is preferentially a dental implant kit.

By means of the above, it will be possible to deliver an implant with the recognised advantages of an internal connection along with an optimal choice for both one-stage and two-stage procedures following the low vertical height of the coronal part. It will also be possible to exclude the expensive pare-mounting on an implant with internal connection by instead providing carrying and insertion function utilising the internal connection as rotational lock and holding means. The invention facilitates production and admits a larger variety of material to be used for the implant body, spacer(s) and tool compared to similar products as shown by prior art since thin wall sections are being avoided to a much larger extent.

In a yet further aspect of the invention, the implant reduces the risk of abutment screw loosening with press- or friction-fit and also benefits from a strong but still controlled flexible abutment connection.

The proposed technique of this aspect of the invention is metal deformation of a thin section or sections of the implant indexing region and/or the internal abutment connection.

Thus according to this aspect of the invention we provide an implant for a tightly fitting prosthesis, said implant comprising an externally threaded implant body intended to be screwed into bone using an insertion tool, the body being provided with an internal open ended axial bore and an indexing region at the open end of the bore, the indexing region being provided with a connection to support a spacer element and having means for co-operating with the spacer element to prevent twisting between the spacer element, the implant body and the insertion tool characterised in that that the implant comprises a deformation zone.

In this aspect of the invention it is preferred that it is the spacer which comprises the deformation zone. Preferably, the deformation zone is provided on one or both sides of each non-rotational means. In a preferred aspect of the invention, the deformation zone comprises a "pointed" angle, for example, an (internal) acute angle, e.g. of less than 90 degrees.

We especially provide an implant as hereinbefore described wherein it is the connection elements, the internal connection posts which are adapted to avoid excessive bending. In this aspect of the invention the metal deformation may be in the implant connection and/or the internal abutment connection. In particular, the corners of the connection posts or elements are deformed in order to minimise rotational movements.

In a yet further alternative it is the corners of the guidance portion that us deformed.

The material of choice for the implant and in some cases the abutment is titanium, which is highly work hardenable and thus enables the making of a thin deformed section or ridge even stronger than the original material.

In an especially preferred embodiment of the invention we provide an implant for a tightly fitting prosthesis, said implant comprising an externally threaded implant body intended to be screwed into bone using an insertion tool, the body being provided with an internal open ended axial bore and an indexing region at the open end of the bore, the indexing region being provided with a connection to support a spacer element and having means for co-operating with the spacer element to prevent twisting between the spacer element, the implant body and the insertion tool characterised in that that implant comprises a deformation zone and the axial length of the indexing region does not overlap with the external thread as hereinbefore described.

We especially provide a spacer as hereinbefore described which also comprises a deformation zone.

Other advantages and features will be readily available from the following description of the preferred embodiments, the drawings and claims.

The invention will now be described with reference to the accompanying drawings in which FIG. 1 is a partial longitudinal cross sectional view with portions in elevation for purposes of illustration of a implant body of an implant according to the present invention;

FIG. 2 is a partial cross sectional view with portions in elevations for purpose of illusion of a spacer with a fastening head for a dental prosthesis for the implant of FIG. 1;

FIG. 3a is an end view of the implant body of FIG. 1;

FIG. 3b is an end view of a spacer of FIG. 2;

FIG. 4a is an end view of a first modification of the implant body of FIG. 1;

FIG. 4b is an end view of a first modification of the spacer of FIG. 2;

FIG. 5a is an end view of the second modification of the implant body of FIG. 1;

FIG. 5b is a second modification of the spacer of FIG. 2;

FIG. 6 is a side view of the tool by means of which an implant body according to FIG. 1 can be screwed into a hole in the bone;

FIG. 7 is a side view and particular cutaway view of the front parts of the tool where the tool exerts a support function on an implant body according to FIG. 1.

Figure 8:
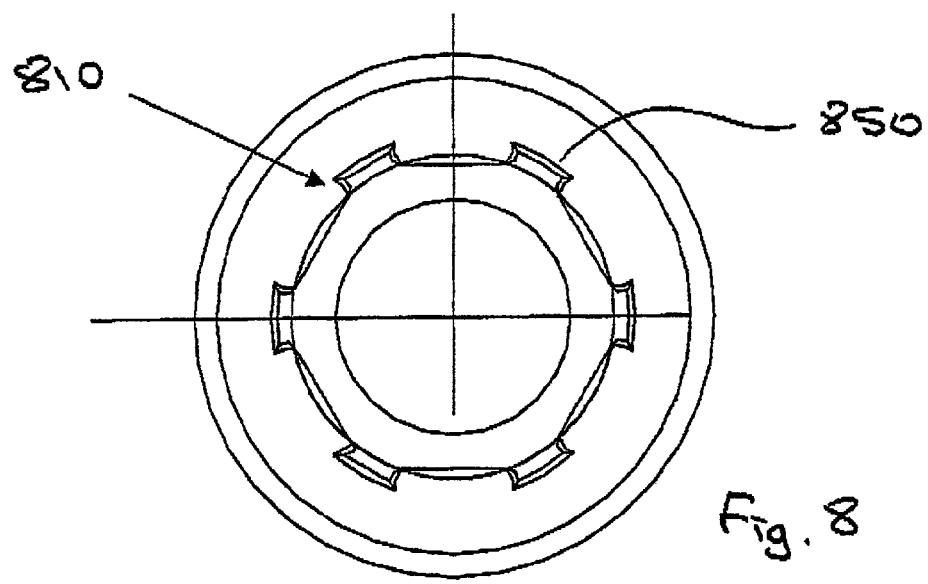
FIG. 8 is an end view of a deformable implant body.

The principles of the present invention are particularly useful when incorporated into an implant, for example, an orthopaedic implant, such as a dental implant, of an embodiment of the implant body generally indicated at 10 in FIG. 1 which acts with a spacer generally indicated at 32 in FIG. 2. The implant body 10 is of a type with external thread(s).

The implant body 10, which is closed at its one end or cervical end which is at the bottom of FIG. 1 has towards a coronal end at the top an open blind bore 11. Near the closed end, the blind bore 11 is provided with internal threads 12 with a relatively small diameter in which can be screwed an spacer screw which is not shown in FIG. 1 and which will be discussed hereinafter. The implant body 10, exhibits an outer substantially cylindrical portion 16 between the coronal front edge 22 and the external thread 18.

To the internal threads 12 of the implant body 10 is connected in the coronal direction a guidance and centering area 20 which is a cylindrical larger diameter portion than the internal threads 12 and has a smooth, hollow cylindrical inner wall 21. From the guidance and center area 20 to the coronal front edge 22 of the implant body 10 is a positive connection area 24 of the bore 11 in which there are several positive connecting elements in the form of axially extending grooves 26 in an inner wall 27 forming ridges 14. From the front edge 22 to the positive connecting area 24 of the bore 11 has a bevel or chamfer 28 tapering conically in the direction of the cervical or closed end and extending into the vicinity of the positive connecting grooves 26. Between the guidance and centering area 20 and the positive connecting elements or groove 26 there is an annular undercut 30 of minimal height which facilitates a chip deposition-free production of the positive connecting elements or grooves 26.

The spacer 32 as shown in FIG. 2 serves or is incorporated in a tightly fitting prosthesis and is provided with an all around attachment shoulder 34 for the prosthesis which may be a crown of a tooth. The spacer 32 has an annular shoulder 36 which connects the fastening end to a stub or plug portion which is received in the blind bore 11 of the implant body 10. The stub or plug portion has immediately adjacent the shoulder 36 a positive connection portion 38 followed by a guidance and centering portion 40 which will be received in the blind bore with the shoulder 36 engaging the front edge 22. The positive connection area 38 has a plurality of axially directed positive connection noses 46 whose shape and arrangement but not necessarily the number corresponds to the positive connection grooves 26 of the implant body 10. The positive connection area 38 of the spacer 32 is provided with an annular undercut 48 between the shoulder 36 and the positive connecting noses 46 and this facilitates the chip deposition during manufacture of the positive connecting noses 46.

When inserting the spacer 32, which is provided with the axial longitudinal bore 33 whose internal diameter corresponds to the external diameter of a not shown spacer screw, is inserted in the implant body 10, the guidance and centering portion 40 which is formed by a cylindrical guidance and centering collar 44, will be engaged in the guidance and centering area 20 so that a smooth cylindrical circumferential surface of the guidance and centering portion 40 comes to rest on the inner cylindrical surface 21 of the guidance and centering area 20 of the implant body 10. At the same time positive connection portion 38 engage in the positive connection grooves 26 while the shoulder 36 comes to rest on the front edge 22. Therefore, the spacer 32 is connected to the implant body 10 in a twist preventing manner. By means of the spacer screw traversing the spacer 32 and being screwed into the internal threads 12 of the implant body 10, the spacer 32 can be firmly connected to the implant body 10.

As shown in FIG. 3*a*, the positive connecting area of the implant body 10 has six equally positive connecting grooves 26 which in the represented embodiment have a cross sectional shape of a rectangle with a substantially tangential directed but also curved longitudinal edges and have an annular spacing of 60° between centres of adjacent grooves. In FIG. 3*b*, the spacer 32 in the embodiment of FIGS. 1 and 2 is provided with six equally spaced, axial positive connecting noses 46. In the embodiments of FIGS. 4*a* and 4*b*, the implant body 10' in FIG. 4*a* has twelve positive connecting grooves 26' with an equal annular spacing of 30° and in FIG. 4*b* the spacer 32' is only provided with four positive connecting noses 46'. The positive connecting grooves 26' and the positive connecting noses 46' have in this case a triangular cross section in a plane perpendicular to the longitudinal axes of the implant body and of the spacer. It is pointed out that the spacer 32' has only four positive connecting noses 46 which have a 90 degree annular spacing therebetween.

In the embodiment of FIGS. 5*a* and 5*b*, the implant body 10" of FIG. 5*a* has twelve positive connecting grooves 26" with a 30 degree spacing and the grooves 26" have a circular segmental cross section in a plane perpendicular to the longitudinal axis of the implant body 10". According to FIG. 5*b*, the spacer 32" is provided with six positive connecting noses 46" each having a corresponding cross section to the cross section of the grooves 26".

As a function of the spacing or the spacing ratio of the implant body 10' and 10" relative to the spacers 32' and 32", the spacers 32' and 32" can be inserted in different rotational positions within their respective basic bodies 10' and 10". Thus, the treating surgeon has a number of desired positions available to him as far as orienting the spacer such as 32' relative to the implant body 10'.

The axial grooves 26 apart from being twisting preventing means for the spacer also arranged to be used as a connection for a tool which is described below. FIG. 6 shows a tool part 49 which can be coupled to an electrically operated or otherwise operated (pneumatically, hydraulically, etc.) motor (not shown) or hand driven handle via its upper part 50 which has an attachment for the drive motor or handle. At its other end, the tool is provided with recesses (grooves) 51 for forming wing shaped elements 50. A cone angle α is chosen a about 4-6°.

FIG. 7 shows the cooperation between the tool 49 and the positive connection area 24 of the implant body. By means of a cone shape on the front part 52 of the tool, a bearing function of the implant body 10 is obtained via axial grooves. The number of recesses and wings in this embodiment is six each but other embodiments can have a number of recesses less than the axial grooves. The wings correspond in terms of shape with grooves 26 in the positive connection area 24 of the implant body.

Another embodiment is when the inner tool surface 53 has conical shape and the bearing function is conducted though interaction with the most coronal part of the ridges 14 and the inner surface 27.

Although modifications and changes may be suggested by those versed in the art, it should be understood that we wish to embody within the scope of the patent granted herein all such modifications that reasonably and properly come within the scope of our contribution to the art.

Referring to FIG. 8, the connecting area of the implant body (810) has six equally spaced, axial positive connecting noses (850) which in the represented embodiment have a cross sectional shape of a deformable rectangle and an annular spacing of 60° between centres of adjacent noses.

Figure 9:
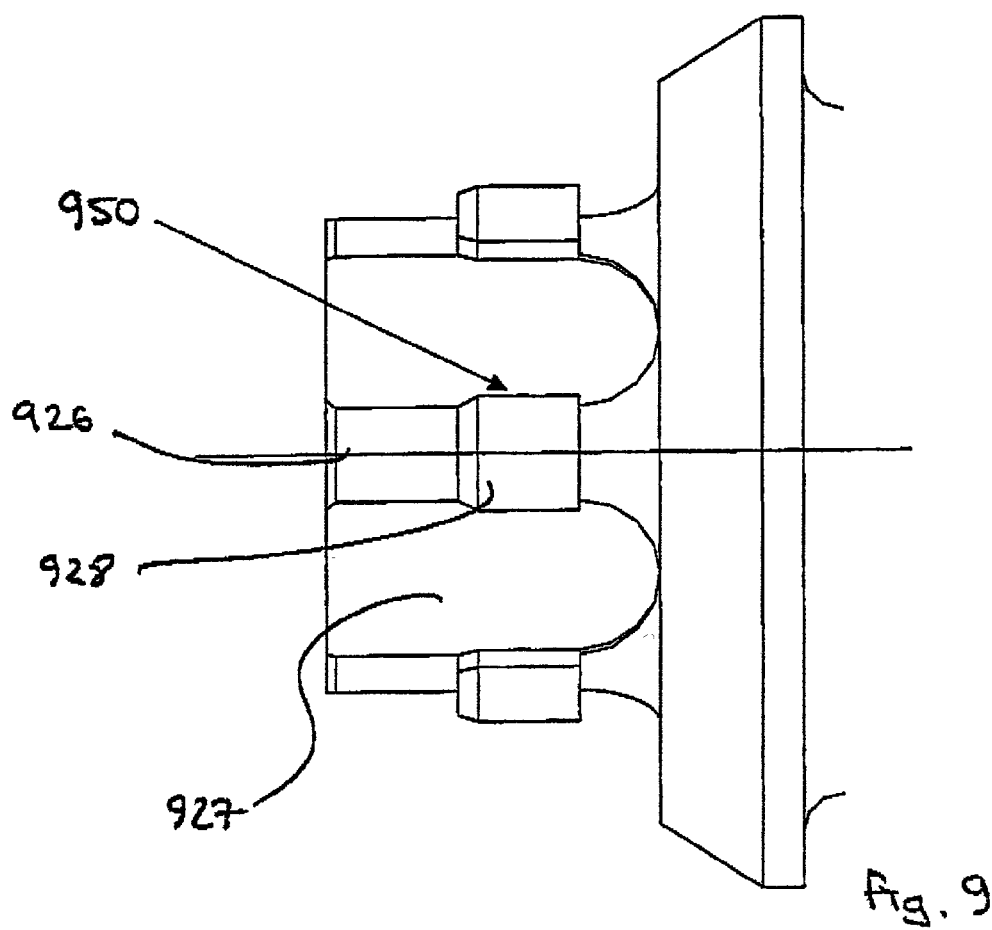
FIG. 9 is a side view of a deformable implant body.

Referring to FIG. 9, the connecting noses (950) comprise a flange (928) on the side of ridges (926) between each of the grooves (927).

Figure 10:
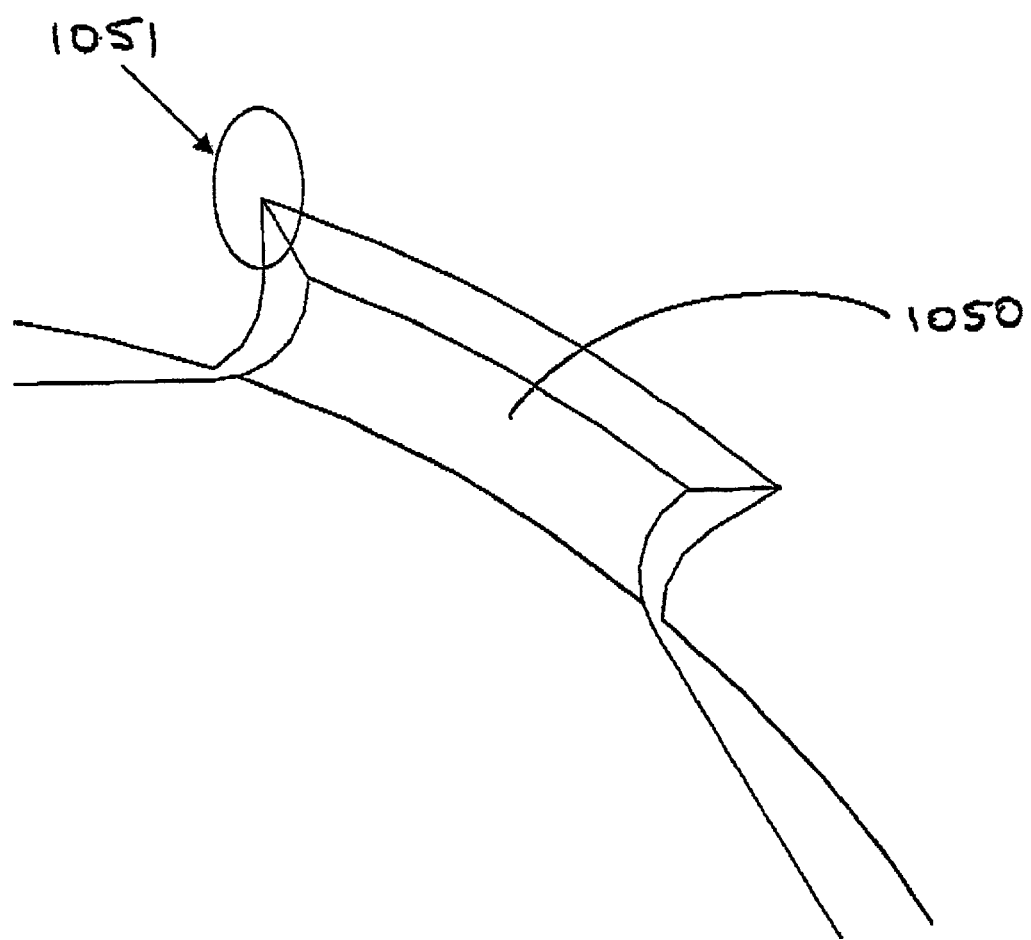
FIG. 10 is a high resolution view of a deformable implant body.

Referring to FIG. 10, a corner (1051) of the nose (1050) is deformable from an acute (internal) angle.

The invention claimed is:

1. An implant for a tightly fitting prosthesis, said implant comprising:
   an externally threaded implant body having a coronal portion and an external thread, the implant body intended to be screwed directly into bone through the use of the external thread using an insertion tool, the body being provided with an internal open ended axial bore having an indexing region comprising a positive connection region at the open end of the bore,
   wherein the positive connection region comprises a connection to support a spacer and for connection to the insertion tool, the positive connection region having means for cooperating with the spacer and the insertion tool to prevent twisting between the spacer and the implant body or the insertion tool and the implant body,
   wherein the indexing region also comprises a cylindrical guidance and centering region for guiding and centering a plug portion of the spacer during connection of the spacer to and retention within the implant body, the guidance and centering region being located between the positive connection region and an internally threaded region of said axial bore;
   wherein the axial length of the indexing region extends within the coronal portion and does not overlap with the external thread; and
   wherein the indexing region comprises a plurality of axially extending grooves and ridges for cooperation with the insertion tool to permit the insertion tool to provide a carrying function for positioning the implant.

2. An implant according to claim 1 wherein the spacer supporting connection comprises at least three connecting elements.

3. An implant according to claim 1 wherein said guidance and centering region is towards one end of the indexing region.

4. An implant according to claim 1 wherein the implant comprises at least one spacer, having an axially extending passage being fastenable at one end to a coronal front edge of the implant body.

5. An implant according to claim 4 wherein the spacer is attachable by means of a spacer screw traversing the spacer and being screwed into the bore of the implant body.

6. An implant according to claim 4 wherein the spacer has a fastening end for a prosthetic construction spaced from a plug portion by an annular shoulder.

7. An implant according to claim 6 wherein the plug portion is adjacent the annular shoulder and has a positive connecting region, with at least one connecting element, a guidance and centering region inside.

8. An implant according to claim 7 wherein the guidance and centering region of the plug portion of the spacer has an outer diameter essentially matching the diameter of the guidance and centering region of the implant.

9. An implant according to claim 8 wherein as the shoulder of the spacer engages the coronal front edge of the implant body the guidance and centering regions of the spacer are received in the guidance and centering region of the indexing region and a positive connection region of the spacer being disposed in the positive connection region of the indexing region.

10. An implant according to claim 1 wherein at least one connecting element of the implant body has a shape of a positive connecting groove open toward one end and extending substantially parallel to the longitudinal axis of the implant body.

11. An implant according to claim 10 wherein the implant body has a plurality of connecting elements, said connecting elements being spaced around the circumference of the indexing region of the implant body with an annular spacing of 30°.

12. An implant according to claim 10 wherein the implant body has a plurality of connecting elements, said elements being spaced around a circumference of the indexing region with an annular spacing of 60°.

13. An implant according to claim 10 wherein the positive connecting groove has a substantially circular segmental cross section in a plane extending perpendicular to the axis of the bore of the implant body.

14. An implant according to claim 10 wherein the positive connecting groove has a substantially triangular cross section in a plane extending perpendicular to the axis of the bore.

15. An implant according to claim 10 wherein the positive connecting groove has an approximately rectangular-curved cross section in a plane extending perpendicular to the axis of the bore.

16. An implant according to claim 15 wherein the positive connection region of the implant body has an annular undercut between each of the plurality of connecting elements and the guidance region.

17. An implant according to claim 10 wherein the positive connecting groove is open toward the open end of the bore of the implant body.

18. An implant according to claim 10 wherein the positive connecting groove has an at least partially decreasing cross section from the open end towards the closed end of the bore.

19. An implant according to claim 18 wherein the cross section of the positive connecting groove decreases radially from the open end to the closed end of the bore.

20. An implant according to claim 1 wherein the implant body has a plurality of connecting elements spaced around a periphery of the indexing region and the spacer has a plurality of connecting elements spaced around a positive connection region thereof with a number of connecting elements of the spacer being less than a number of connecting elements for the implant body.

21. An implant according to claim 1 wherein an inner end wall of the implant body at one end has a bevel tapering conically towards a closed end from a coronal front edge of the implant body into the positive connection region of the implant body.

22. An implant according to claim 21 wherein the spacer has an annular undercut between an annular shoulder and each of a plurality of connecting elements.

23. An implant according to claim 1 wherein the implant is a dental implant.

24. An implant according to claim 1 wherein the implant is a titanium implant.

25. An arrangement for implanting a prosthesis comprising:

an implant adapted to permit application of a screwing force applied by an insertion tool for positioning and securing the implant directly into bone, the implant comprising an externally threaded implant body having a coronal portion and an external thread, the implant body, the body having an internal open ended axial bore having an indexing region comprising a positive connection region at the open end of the bore; and at least one spacer element adapted to be supported against a contact surface of the implant, wherein the positive connection region of the implant comprises a connection to support the spacer element and for connection to an insertion tool, the positive connection region having means for cooperating with the spacer element and the insertion tool for preventing twisting between the spacer element and the implant body or for preventing twisting between the insertion tool and the implant body, wherein the indexing region of the implant also comprises a cylindrical guidance and centering region for guiding and centering a screw insertable through the spacer element during connection of the spacer element to and retention within the implant body, the guidance and centering region being located between the positive connection region and an internally threaded region of the axial bore, wherein the axial length of the indexing region extends within the coronal portion and does not overlap with the external implant thread, and wherein the means for cooperating with the spacer element and the insertion tool comprises a plurality of axially extending grooves and ridges in the indexing region.

26. An arrangement according to claim 25, wherein a relatively large force applied, by means of the insertion tool, on the means for cooperating with the spacer element and the insertion tool, is prevented from mechanically deforming the latter fitting between the implant and the spacer element to a non-fitting situation.

* * * * *

UNITED STATES PATENT AND TRADEMARK OFFICE
CERTIFICATE OF CORRECTION

| | |
|---|---|
| PATENT NO. | : 7,309,231 B2 |
| APPLICATION NO. | : 10/117310 |
| DATED | : December 18, 2007 |
| INVENTOR(S) | : Engman |

It is certified that error appears in the above-identified patent and that said Letters Patent is hereby corrected as shown below:

In the claims

Column 12, lines 21-57, Please amend claim 25 as follows:

25. An arrangement for implanting a prosthesis comprising: an implant adapted to permit application of a screwing force applied by an insertion tool for positioning and securing the implant directly into bone, the implant comprising an externally threaded implant body having a coronal portion and an external thread, the implant body, the body having an internal open ended axial bore having an indexing region comprising a positive connection region at the open end of the bore; and at least one spacer element adapted to be supported against a contact surface of the implant, wherein the positive connection region of the implant comprises a connection to support the spacer element and for connection to an insertion tool, the positive connection region having means for cooperating with the spacer element and the insertion tool for preventing twisting between the spacer element and the implant body or for preventing twisting between the insertion tool and the implant body, wherein the indexing region of the implant also comprises a cylindrical guidance and centering region for guiding and centering a screw insertable through the spacer element during connection of the spacer element to and retention within the implant body, the guidance and centering region being located between the positive connection region and an internally threaded region of the axial bore, wherein the axial length of the indexing region extends within the coronal portion and does not overlap with the external implant thread, and wherein the means for cooperating with the spacer element and the insertion tool comprises a plurality of axially extending grooves and ridges in the indexing region.

Signed and Sealed this
Twentieth Day of October, 2015

Michelle K. Lee
*Director of the United States Patent and Trademark Office*